(12) United States Patent
Kessel et al.

(10) Patent No.: US 6,509,497 B1
(45) Date of Patent: Jan. 21, 2003

(54) PROCESS FOR PREPARING GUANIDINE DERIVATIVES

(75) Inventors: Knut Kessel, Mannheim (DE); Michael Kluge, Ludwigshafen (DE); Thomas Bogenstätter, Bad Dürkheim (DE); Günter Scherr, Ludwigshafen (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 09/499,444

(22) Filed: Feb. 7, 2000

(30) Foreign Application Priority Data

Feb. 11, 1999 (DE) .......................................... 199 05 711

(51) Int. Cl.$^7$ ............................................. C07C 241/00
(52) U.S. Cl. ..................................................... 562/560
(58) Field of Search .......................................... 562/560

(56) References Cited

U.S. PATENT DOCUMENTS 5,719,319 A * 2/1998 Weiss et al. ................. 562/560

FOREIGN PATENT DOCUMENTS

EP 754 679 1/1997

* cited by examiner

*Primary Examiner*—Alan L. Rotman
*Assistant Examiner*—Binta Robinson
(74) *Attorney, Agent, or Firm*—Keil & Weinkauf

(57) ABSTRACT

A process for preparing guanidine derivatives, in particular creatine, is described and entails continuously combining a cyanamide derivative and a primary or secondary amine in the presence of crystals of the guanidine derivative.

8 Claims, No Drawings

PROCESS FOR PREPARING GUANIDINE DERIVATIVES

The present invention relates to a process for preparing guanidine derivatives of the formula I

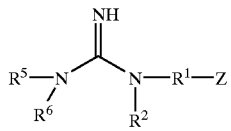

in which
- $R^1$ is $C_1$–$C_8$-alkylene or a divalent cycloaliphatic radical having 5 to 10 carbon atoms,
- $R^2$ is H or $C_1$–$C_8$-alkyl, or
- $R^1$ and $R^2$ represent, together with the N atom to which they are bonded, a 5- or 6-membered Z-substituted ring,
- Z is $COOR^3$, $SO_2OR^3$ or $PO(OR^3)(OR^4)$,
- $R^3$ is in each case independently H, one equivalent of an alkali metal or alkaline earth metal,
- $R^4$ is H, one equivalent of an alkali metal or alkaline earth metal or $C_1$–$C_6$-alkyl, and $R^5$ and $R^6$ are independently H or $C_1$–$C_8$-alkyl, by reacting a cyanamide derivative of the formula II

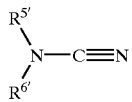

in which $R^{5'}$ and $R^{6'}$ are independently H, the equivalent of an alkali metal or alkaline earth metal or $C_1$–$C_8$-alkyl, with an amine of the formula III

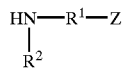

in which $R^1$, $R^2$ and Z have the stated meanings.

The invention in particular relates to a process for preparing creatine from cyanamide or its salts and sarcosinate.

Guanidine compounds of the formula I are widespread in nature. Important representatives of this class of substances are, for example, compounds such as arginine and creatine. Creatine occurs in vertebrate muscle tissue, in particular as creatine phosphate, and plays an important part as energy carrier in the cell. Creatine is increasingly being used as dietary supplement to enhance physical performance. Creatine is additionally used for treating disorders of muscle function characterized by increased creatine excretion in the urine.

EP-A 0754679 describes a process for preparing creatine by reacting cyanamide with sodium or potassium sarcosinate. The reaction is carried out batchwise, and it is stated that this is usually complete after 2–5 h. The batchwise process is disadvantageous because the batches of reaction product, which results in the form of an aqueous suspension, must either be worked up batchwise as they are produced or be stored temporarily in stirred buffer tanks. Batchwise synthesis is moreover staff-intensive and susceptible to errors. In addition, an unwanted reduction in the yield of product arises because the creatine-saturated washing water is not recycled to the process.

It is an object of the present invention to develop the process mentioned at the outset further so that guanidine derivatives of the formula I are obtained continuously in high purity and in high yield in a simple manner.

We have found that this object is achieved by continuously combining the cyanamide derivative of the formula II with the amine of the formula III in the presence of seed crystals of the guanidine derivative of the formula I. "Continuous combination" means that the addition of the reactants takes place in such a way that the ratio of concentrations of the reactants—apart, where appropriate, from the start-up phase—in the reaction mixture is essentially constant over the time taken for the reaction. This is not the case in particular when one reactant is introduced first and the other reactant is metered in over a lengthy period.

The novel process makes use of a cyanamide derivative of the formula II. These are—as in the case of cyanamide and its salts—commercially available or the synthesis thereof is well known to the skilled worker.

$R^5$ and $R^6$ in formula I are independently H or branched or unbranched $C_1$–$C_8$-alkyl, in particular methyl, ethyl, n-propyl, 1-methylethyl, n-butyl, 1-methylpropyl, 2-methylpropyl, 1,1-dimethylethyl, n-pentyl, 1-methylbutyl, 2-methylbutyl, 3-methylbutyl, 2,2-dimethylpropyl, 1-ethylpropyl, n-hexyl, 1,1-dimethylpropyl, 2,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl, 1-ethyl-2-methylpropyl, n-heptyl, n-octyl, with $C_1$–$C_4$-alkyl such as methyl, ethyl, propyl, isopropyl, butyl being preferred. Preference is given to $R^5=R^6=H$.

$R^{5'}$ and $R^{6'}$ in formula II have the meanings stated for $R^5$ and $R^6$ respectively and may additionally be the equivalent of an alkali metal or alkaline earth metal. Particular preference is given to $R^5=R^{6'}=H$ or $R^{5'}=H$ and $R^{6'}$=alkali metal or $R^{5'}$ and $R^{6'}$ together are an alkaline earth metal, in particular calcium. Cyanamide is the most preferred cyanamide derivative of the formula II.

The other starting material employed is an amine of the formula III. $R^1$ is a branched or unbranched $C_1$–$C_8$-alkylene radical, preferably methylene, ethylene, n-propylene, 1-methylethylene, n-butylene, 1-methylpropylene, 2-methylpropylene, 1,1-dimethylethylene, n-pentylene, 1-methylbutylene, 2-methylbutylene, 3-methylbutylene, 2,2-dimethylpropylene, 1-ethylpropylene, n-hexylene, 1,1-dimethylpropylene, 2,2-dimethylpropylene, 1-methylpentylene, 2-methylpentylene, 3-methylpentylene, 4-methylpentylene, 1,1-dimethylbutylene, 1,2-dimethylbutylene, 1,3-dimethylbutylene, 2,2-dimethylbutylene, 2,3-dimethylbutylene, 3,3-dimethylbutylene, 1-ethylbutylene, 2-ethylbutylene, 1,1,2-trimethylpropylene, 1,2,2-trimethylpropylene, 1-ethyl-1-methylpropylene, 1-ethyl-2-methylpropylene, n-heptylene, n-octylene or a divalent cycloaliphatic radical having 5 to 10 carbon atoms, such as 1,2-, 1,3-, 1,4-cyclohexylene, 1,2- or 1,3-cyclopentylene or radicals of the following structure:

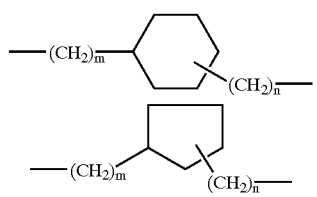

in which n and m may assume the values 0, 1 or 2, with the proviso that n and/or m is different from 0. The cycloaliphatic radicals may be in either the cis or the trans configuration. $C_1$–$C_6$-alkylene such as methylene and ethylene are preferred.

The $R^1$ radical may be substituted by one or more, for example 1 to 3, substituents selected from an optionally protected amino, hydroxyl or cyano group.

$R^2$ is H or $C_1$–$C_8$-alkyl, preferably H, methyl or ethyl. Z is $COOR^3$, $SO_2OR^3$, or $PO(OR^3)(OR^4)$, in which $R^3$ is in each case independently H, an alkali metal such as sodium or potassium, or one equivalent of an alkaline earth metal such as calcium, and $R^4$ is H, an alkali metal, one equivalent of an alkaline earth metal or $C_1$–$C_6$-alkyl.

The amine of the formula III is preferably an amino carboxylic acid, amino sulfonic acid or amino phosphonic acid or a salt thereof. Sarcosine, in particular in the form or sodium or potassium sarcosinate, and glycine, taurine or 4-aminomethylcyclohexanecarboxylic acid are particularly preferred.

According to the invention, the cyanamide of the formula II and the amine of the formula III are continuously brought into contact with one another in the presence of seed crystals of the guanidine derivative of the formula I. Thus, for example, a stream of the cyanamide derivative, preferably in the form of an aqueous solution, can be mixed with the seed crystals, and the resulting suspension can be reacted with the amine of the formula III, preferably in the form of an aqueous solution. On the other hand, the amine of the formula III can be mixed with the seed crystals, and then be mixed with the cyanamide derivative. In a further alternative, the seed crystals can be converted into a suspension, and the cyanamide derivative of the formula II and the amine of the formula III are combined with the suspended seed crystals.

The cyanamide derivative of the formula II and the amine of the formula III are preferably employed in a molar ratio of from 2:1 to 1:2, in particular from 0.8:1 to 1.1:1.

The novel reaction normally takes place in an aqueous medium such as water itself or a mixture of water with water-miscible organic solvents such as alcohols, for example methanol or ethanol; acetone or THF. The cyanamide derivative of the formula II and the amine of the formula III can be employed in the form of solutions in water or said water-miscible solvents or mixtures thereof.

The novel reaction preferably takes place at a pH of from 8 to 12, in particular 9 to 10. To maintain a pH in the stated range, it is normally necessary to introduce an acid or base, depending on the nature of the cyanamide derivative of the formula II employed and of the amine of the formula III, into the reaction medium.

Examples of suitable acids are organic acids such as formic acid and acetic acid, inorganic acids such as hydrochloric acid, sulfuric acid and phosphoric acid, and, in particular, carbon dioxide in gaseous or solid form.

Bases suitable for adjusting the pH are, in particular, NaOH, KOH, LiOH or $Ca(OH)_2$.

The introduction of the acid or base can be controlled according to requirements. For this purpose, the current pH of the reaction medium is measured by a continuously operating pH measurement and compared with a preset pH, and the amount of acid or base necessary to correct the pH is added. The measured pH can be provided, for example, in the form of an electronic signal, which is compared with a preset value by an electronic data processor which automatically calculates the necessary amount of acid or base and controls a metering system.

In a particularly preferred embodiment of the acid metering, the pH is adjusted by adding carbon dioxide to an aqueous solution of the amine of the formula III, and using this solution for reaction with the cyanamide derivative. The addition of carbon dioxide takes place, for example, by passing in $CO_2$ gas or adding dry ice. This variant is particularly preferred in cases where the solution employed of the amine of the formula III has a pH which is higher than the desired pH in the reaction medium. One example thereof is a technical solution of sarcosine/sarcosinate which is prepared by basic hydrolysis of sarcosine nitrile and usually has a greater or lesser excess of base. In the amine solution to which carbon dioxide has been added, an equilibrium with the corresponding carbamate is set up. On reaction with the cyanamide derivative of the formula II, the liberated hydroxide ions are very substantially consumed by cleaving the carbamate again, so that the system is self-buffering and no external pH control is necessary. In the case where the amine of the formula III is sodium or potassium sarcosinate in the form of an aqueous solution, the latter can be adjusted with carbon dioxide for example to a pH of from 8 to 12, in particular from 9 to 10, and continuously combined with a cyanamide derivative of the formula II, for example cyanamide.

The novel process preferably takes place at a temperature of from +20 to 150° C., preferably 40 to 100° C., in particular 60 to 80° C. The reaction between the cyanamide derivative of the formula II and the amine of the formula III is slightly exothermic. To maintain the stated temperature it is therefore usually necessary to heat the reaction medium. This expediently takes place using suitable heat exchanger devices. Alternatively, part of the reaction medium can be continuously circulated through a temperature-controlled zone by a pump. The residence times in the reactor in the novel process are generally from 0.5 to 48, preferably 2 to 36, very particularly preferably 4 to 24, hours.

The novel process can be carried out under elevated pressure, atmospheric pressure or reduced pressure, for example under an absolute pressure down to 10 mbar. Atmospheric pressure is generally preferred. Reduced pressure may be advantageous in order to remove the ammonia which is formed as byproduct of the reaction from the reaction mixture.

In the novel process, cyanamide of the formula II and amine of the formula III are continuously combined in the presence of seed crystals of the guanidine derivative of the formula I. The crystals of guanidine derivative which have grown can be removed continuously or batchwise.

Suitable for carrying out the novel process are conventional reactors such as, in particular, a continuous stirred vessel reactor or a cascade of stirred vessels. It is expedient to ensure thorough mixing of the reactants in the reaction chamber.

The advantage of the continuous process is that essentially constant concentrations of the reactants and an essentially constant amount of guanidine derivative of the formula I dissolved in the reaction medium are present in the reaction medium. It is possible in this way to maintain an essentially constant, controllable degree of supersaturation and thus a controlled rate of crystallization of the guanidine derivative of the formula I. The control of the rate of crystallization of the guanidine derivative of the formula I means that it is possible to obtain products of high purity with a substantially uniform particle distribution and average particle sizes of, for example, above 150 μm. This makes it possible to reduce the resistance of the suspension on filters to values of, for example, less than $10 \times 10^{12}$ mPa·s·m$^{-2}$ and achieve practicable filtration times. The resulting crystals usually have sufficiently high purity so that they can be used, where appropriate after washing but without further purification, for example as dietary supplements.

In a particularly preferred embodiment, the reaction takes place in a reaction chamber into which cyanamide derivative of the formula II and amine of the formula III are introduced continuously and from which crystals of the guanidine derivative of the formula I are continuously removed, preferably in the form of a crystal suspension. It is expedient to introduce the cyanamide derivative of the formula II and/or the amine of the formula III in the form of aqueous solutions. Crystals of the guanidine derivative of the formula I must always be present in the reaction chamber to act as seed crystals. This can be achieved, for example, by controlling the removal of crystals so that some of them remain as seed crystals in the reaction chamber.

However, to obtain a product with a uniform size distribution which can be predetermined, it is preferred to introduce seed crystals of the guanidine derivative of the formula I, preferably in the form of a suspension, continuously into the reaction chamber. The introduced seed crystals may have an average crystal size and/or crystal size distribution which differs from the removed crystals.

The crystals of the guanidine derivative of the formula I which are removed as product can be subjected to a size classification to obtain a fine material fraction and a coarse material fraction, the fine material fraction being returned as seed crystals to the reaction chamber, and the coarse material fraction being removed from the process as product. The fine material fraction which is suitable as seed crystals has, for example, a particle size distribution of from 1 to <100 μm. The coarse material fraction has, for example, a particle size distribution of from 100 μm to 500 μm. The size classification of the crystals can take place either in suspension or in the dry state. For classification in the dry state, the crystals are previously removed from the mother liquor and dried. The fine material fraction, which has been obtained, for example, by sieving, can be suspended in an aqueous medium for returning to the reaction chamber. Examples of suitable devices for size classification are hydrocyclones and wet sieves for classifying suspended crystals. Examples suitable for classifying dry crystals are cyclones, sieves or sifters.

The amine of the formula III can advantageously be employed in the form of an aqueous solution, for example with a concentration of from 85 to 15, in particular 70 to 30% by weight. An example of a suitable solution is a commercially available aqueous solution of sodium sarcosinate with a content of 40% by weight and a purity of 85–90% by weight.

The introduction of the cyanamide derivative of the formula II and/or of the amine of the formula III or of the aqueous solutions thereof and, where appropriate, necessary acid or base into the reaction medium can expediently take place in such a way that part of the reaction medium is removed from the reaction chamber, mixed with the cyanamide derivative and/or the amine and/or the acid or base and returned to the reaction chamber. The removal, the mixing and the return preferably take place continuously, for example by a pumping reaction medium through a metering and mixing zone into which the cyanamide derivative and/or amine or aqueous solution thereof and/or acid are fed. It is possible in this way expediently to adjust the required concentrations. Local concentration peaks and pH variations can be avoided in this way.

Resuspension of crystals of the guanidine derivative of the formula I which is removed as product stream is subjected to conventional processes, for example filtration or centrifugation, to separate the product from the mother liquor. Suitable devices such as pressure filters, vacuum belt filters, rotating drum filters and skimmer centrifuges are well known to the skilled worker. The removed mother liquor is discharged from the process and, for example, discarded. Discharge of the remaining mother liquor prevents accumulation in the system of byproducts and impurities which are present in the cyanamide derivative of the formula II and/or the amine of the formula III employed.

The crystals removed from the mother liquor can be washed, for example, with cold or hot water. For this purpose, the crystals can be suspended in the washing medium and then removed therefrom. In a preferred aspect of the invention, the washing medium resulting from the washing of the resulting crystals of the guanidine derivative of the formula I is recycled. The washing medium can be used, for example, for predilution or dissolving of the cyanamide derivative or of the amine. The washing medium may also be used for diluting the reaction mixture. On the one hand, this minimizes the water consumption and, on the other hand, the proportion of guanidine derivative of the formula I which dissolves in the washing medium on washing the resulting product is returned to the reaction chamber and is retained in the overall system.

The crystals of the guanidine derivative of the formula I which have been removed from the mother liquor and, where appropriate, washed can then be dried by conventional processes. Suitable examples thereof are flash dryers or fluidized beds. The crystals are expediently dried to a moisture content, which is not bound as water of crystallization, of from 5 to 0% by weight, preferably 2.5 to 0% by weight. It may be advantageous in the specific case to mix the moist crystal cake obtained after removal from the mother liquor with previously dried material in order to prevent caking during drying. Suitable measures for returning dry material are known to the skilled worker.

Depending on the temperature and the ambient humidity, either the anhydrous form or a hydrate is the most thermodynamically stable form of the guanidine derivative of the formula I; additional hydrates with different compositions are obtained where appropriate as metastable structures. In the case of creatine, the monohydrate is the usual form on the market; care must be taken during the drying where appropriate to avoid unwanted overdrying by processes known to the skilled worker.

The steps of separation from the mother liquor, washing and drying advantageously take place continuously in devices suitable for this purpose.

The invention is illustrated in detail by the following example.

EXAMPLE

Continuous Creatine Synthesis in the Presence of Creatine Crystals 150 ml of creatine-saturated washing water and 1 g of creatine monohydrate are introduced into a double-walled glass reactor at 75° C. Then the following streams (i)–(iii) are metered in synchronously and continuously:

(i) 1.5 ml/min of the combined washing liquors from the previous test;
(ii) 1.833 ml/min of an aqueous solution with a volume of 5500 ml prepared by passing about 550 g of carbon dioxide gas into 5375 ml of a 40% strength technical solution of sarcosine sodium salt; this results in pH=9 at 75° C. This corresponds to 4.8 mol of precursor metered in with an average residence time of 10 hours;
(iii) 0.525 ml/min of a 50% strength aqueous solution of cyanamide at 15° C., which corresponds to 4.0 mol of precursor in an average residence time of 10 hours.

The reactor is vigorously stirred and the internal temperature is kept at 75° C. by a thermostat; a constant pH of about 10.0 is set up. As soon as the mixture has reached a volume of 2300 ml, each time about 100 ml of the product suspension are discharged through a valve. After 50 hours, the suspension remaining in the reactor, which has a volume of 2300 ml at 35° C., is cooled and forced under a gauge pressure of 1.5 bar through a sintered metal wire cloth composition plate; the resistance in the pressure filter is $2\times10^{12}$ mPas·m$^{-2}$. The reactor is rinsed with 400 ml of drinking water, and the filter cake is covered therewith; everything is blown dry with a gauge pressure of 0.5 bar for 10 minutes. The residue is suspended twice in 350 ml of drinking water each time and vigorously stirred for 30 minutes each time; in between it is possible to suck dry to a residual moisture content of 10%. The final suspension, which contains about 50% solids, is filtered with suction at room temperature with water-saturated air overnight until creatine remains in the form of its monohydrate. 450 g (3.0 mol) of $H_2N$—C(=NH)—NMe—$CH_2$—COOH×$H_2O$ are obtained, which corresponds to a yield of 62.5% based on sarcosine sodium and 75% based on cyanamide. The content of required product which can be determined by HPLC and titration is greater than 99.5%, and the sulfated ash is less than 0.1%; no caking of the product occurs during drying.

We claim:

1. A process for preparing a guanidine derivative of the formula I

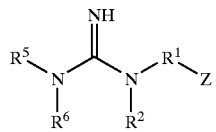

(I)

in which
$R^1$ is $C_1$–$C_8$-alkylene,
$R^2$ is H or $C_1$–$C_8$-alkyl,
Z is $COOR^3$,
$R^3$ is in each case independently H, one equivalent of an alkali metal or alkaline earth metal, and
$R^5$ and $R^6$ are independently H or $C_1$–$C_8$-alkyl,
by reacting a cyanamide derivative of the formula II

(II)

in which $R^{5'}$ and $R^{6'}$ are independently H, the equivalent of an alkali metal or alkaline earth metal or $C_1$–$C_8$-alkyl,
with an amine of the formula III

(III)

in which $R^1$, $R^2$ and Z have the stated meanings,
where the cyanamide derivative of the formula II and the amine of the formula III are continuously combined in the presence of seed crystals of the guanidine derivative of the formula I.

2. A process as claimed in claim 1, wherein the reaction takes place in a reaction chamber into which cyanamide derivative of the formula II and amine of the formula III are continuously introduced, and from which crystals of the guanidine derivative of the formula I are continuously removed.

3. A process as claimed in claim 2, wherein seed crystals of the guanidine derivative of the formula I are continuously introduced into the reaction chamber.

4. A process as claimed in claim 3, wherein the removed crystals are subjected to a size classification to obtain a fine material fraction and a coarse material fraction, with the fine material fraction being returned as seed crystals to the reaction chamber, and the coarse material fraction being discharged from the process as product.

5. A process as claimed in claim 1, wherein the resulting crystals of the guanidine derivative of the formula I are washed with an aqueous medium, and the washing medium is wholly or partly returned to the process.

6. A process as claimed in claim 1, wherein the reaction takes place at a pH of from 8 to 12.

7. A process as claimed in claim 6, wherein the pH is adjusted with $CO_2$.

8. A process as claimed in claim 1, wherein the reaction takes place at a temperature of from 20 to 150° C.

* * * * *